United States Patent
Tonami

(10) Patent No.: US 8,334,885 B2
(45) Date of Patent: Dec. 18, 2012

(54) IMAGE FORMING APPARATUS

(75) Inventor: Kazumasa Tonami, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 414 days.

(21) Appl. No.: 12/704,919

(22) Filed: Feb. 12, 2010

(65) Prior Publication Data
US 2010/0201776 A1 Aug. 12, 2010

(30) Foreign Application Priority Data
Feb. 10, 2009 (JP) .................. 2009-028830

(51) Int. Cl.
*B41J 2/415* (2006.01)
*A62B 7/08* (2006.01)
*G03G 15/00* (2006.01)

(52) U.S. Cl. ............. 347/123; 422/121; 399/38

(58) Field of Classification Search .......... 422/121
See application file for complete search history.

(56) References Cited

U.S. PATENT DOCUMENTS

| | | | |
|---|---|---|---|
| 5,883,934 A * | 3/1999 | Umeda | ............ 378/64 |
| 6,447,731 B1 * | 9/2002 | Sun et al. | ............ 422/121 |
| 7,672,012 B2 * | 3/2010 | Silverbrook | ............ 358/1.8 |
| 8,033,515 B2 * | 10/2011 | Martin et al. | ............ 248/224.61 |
| 2003/0072675 A1 | 4/2003 | Takeda et al. | |
| 2008/0217556 A1 | 9/2008 | Kogawa et al. | |

FOREIGN PATENT DOCUMENTS

| | | |
|---|---|---|
| JP | 2002-058731 | 2/2002 |
| JP | 2003-294280 | 10/2003 |
| JP | 2005-004144 | 1/2005 |
| JP | 2008-251514 | 10/2008 |

* cited by examiner

*Primary Examiner* — Omar Rojas
(74) *Attorney, Agent, or Firm* — Nixon & Vanderhye, P.C.

(57) ABSTRACT

An ion generator for generating positive ions and negative ions is externally attached above a main body of an image forming apparatus. A ratio between positive ions and negative ions which are generated by the ion generator is switched between two ratios in accordance with whether the image forming apparatus is in an operating state or a standby state so that more negative ions are emitted during the operating state. This makes it possible to suppress an effect of an exhaust gas which contains chemical emissions such as an odor and a VOC and which is discharged from the image forming apparatus and to purify an indoor air.

10 Claims, 11 Drawing Sheets

IMAGE FORMING APPARATUS

This Nonprovisional application claims priority under 35 U.S.C. §119(a) on Patent Application No. 2009-028830 filed in Japan on Feb. 10, 2009, the entire contents of which are hereby incorporated by reference.

TECHNICAL FIELD

The present invention relates to an image forming apparatuses such as copying machines, printers, and facsimiles each of which has an ion generator for generating positive ions and negative ions.

BACKGROUND ART

Recently, VOCs (Volatile Organic Compounds) attract attention as a group of causative substances of so-called sick house syndrome which causes health damages such as an allergic symptom, a headache, and/or dizziness. It has been confirmed that a VOC is emitted from image forming apparatuses such as copying machines and printers, personal computers, and the like. In addition to the VOCs, the image forming apparatuses also has a problem of a peculiar odor generated from a heated sheet of recording paper (recording material) and heated toner. In the case of the image forming apparatuses, a VOC and an odor are emitted from a fixing device for fixing a toner image onto a sheet of recording paper.

The image forming apparatuses are indispensable office automation equipment, and installed at most offices. Furthermore, the image forming apparatuses are becoming pervasive also at homes and hospitals. Therefore, many users suffer discomfort due to an exhaust gas which contains volatile chemical substances (chemical emissions) such as a VOC and an odor and which is discharged from the image forming apparatuses.

In view of this, for example, Patent Literature 1 discloses the following art. A blower fan, a negative ion generating section, a positively-charged filter, etc. are provided inside an image forming apparatus. Toner powder and dust generated inside the image forming apparatus are negatively charged so that they are adsorbed to the positively-charged filter, thereby reducing such harmful substances to be discharged outside the image forming apparatus. In addition, dust, mold, etc. which are about to externally intrude into the image forming apparatus are negatively charged so as to be also adsorbed to the positively-charged filter, thereby suppressing intrusion of such harmful substances from outside the image forming apparatus.

In Patent Literature 2, the applicant of the present application has proposed electronic devices such as personal computers, copying machines, and printers in each of which an ion generating section for removing chemical emissions such as a VOC and an odor from an atmosphere is provided so that emission of the chemical emissions is suppressed. As for the electronic devices, the applicant has also proposed an arrangement in which adhesion of dust etc. to the ion generating section is suppressed by providing a filter at an upstream of the ion generating section in a ventilation direction.

On the other hand, air purifiers for purifying an indoor air are becoming pervasive at offices, homes, hospitals, etc. For example, an art of Patent Literature 3 makes it possible to effectively remove floating bacteria in the air by using positive ions and negative ions which are generated at a time.

Citation List
  Patent Literature 1
    Japanese Patent Application Publication (Tokukai, No. 2005-004144 A (Publication Date: Jan. 6, 2005))
  Patent Literature 2
    Japanese Patent Application Publication (Tokukai, No. 2008-251514 A (Publication Date: Oct. 16, 2008))
  Patent Literature 3
    Japanese Patent Application Publication (Tokukai, No. 2002-58731 A (Publication Date: Feb. 26, 2002))

SUMMARY OF INVENTION

Technical Problem

Unfortunately, in the case of Patent Literature 1, it is necessary to provide in the image forming apparatus a negative ion generating section, a positively-charged filter, etc. which are not directly related to a copying process of the image forming apparatus. This has caused increases in the size and cost of the image forming apparatus.

Also in the case of Patent Literature 2, an ion generating section is provided inside the housing of the image forming apparatus. This also causes an increase in the size of the image forming apparatus.

In the case of Patent Literature 3, it is possible to purify an indoor air but is not possible to purify the exhaust gas of the image forming apparatus.

Further, it is very uneconomical to provide both a high-cost image forming apparatus such as the one disclosed in Patent Literature 1 or 2 and an air purifier such as the one disclosed in Patent Literature 3.

However, the applicant of the invention found that, depending on a method of emitting ions, it was possible to suppress an effect of an exhaust gas even though, unlike Patent Literatures 1 and 2, a negative ion generating section, a filter, and the like were not provided inside an image forming apparatus and ions are generated and emitted outside the image forming apparatus. Such a change of an idea made it possible to realize that image forming apparatus of the present invention which can suppress the effect of the exhaust gas from the image forming apparatus and can purify an indoor air.

Solution to Problem

An object of the present invention is to provide an image forming apparatus which can suppress an effect of that exhaust gas containing a chemical emission emitted from the image forming apparatus, and can purify an indoor air.

In order to attain the object, an image forming apparatus of the present invention is an image forming apparatus for forming an image on a recording material, including: an ion generator, provided outside a main body of the image forming apparatus, for generating and emitting positive ions and negative ions; an emission direction changing section for changing, in accordance with whether the image forming apparatus is in an operating state or a non-operating state, a direction of ion emission from the ion generator; and an emission amount adjusting section for changing, in accordance with whether the image forming apparatus is in the operating state or the non-operating state, a ratio between positive ions and negative ions to be emitted from the ion generator so that more negative ions are emitted in the operating state than in the non-operating state.

According to the arrangement, the emission direction changing section changes the emission direction in accordance with whether the image forming apparatus is in the operating state or the non-operating state. In the operating state of the image forming apparatus, an exhaust gas is generated. Accordingly, it is preferable to set an emission direction to the one in which an odor of the exhaust gas is effectively neutralized. In the non-operating state of the image forming apparatus, no exhaust gas is generated. Accordingly, it is preferable to set an emission direction to the one in which floating bacteria in the air are effectively removed. That is, the arrangement allows the image forming apparatus to perform two functions of suppressing the effect of the exhaust gas of the image forming apparatus and purifying an indoor air. In the present Description, the operating state of the image forming apparatus refers to a state in which the image forming apparatus carries out print processing, and the non-operating state of the image forming apparatus refers to a state in which the power of the image forming apparatus is ON and in which the image forming apparatus does not carry out print processing.

In addition, according to the arrangement, the ion generator is provided outside the main body of the image forming apparatus. This makes it possible to prevent an increase in the size of the main body, and eliminate the need for an additional air purifier. As a result, an indoor space can be effectively used.

For example, positive ions and negative ions are generated and emitted by the ion generator at a time. Such positive ions and negative ions are preferable for the present invention because they can effectively remove floating bacteria in the air and can effectively neutralize an odor of the exhaust gas of the image forming apparatus.

Furthermore, according to the arrangement, the emission amount adjusting section changes, in accordance with whether the image forming apparatus is in the operating state or the non-operating state, a ratio between positive ions and negative ions to be emitted from the ion generator so that more negative ions are emitted in the operating state than in the non-operating state. In the operating state, an exhaust gas containing chemical emissions such as a VOC and an odor is generated. Accordingly, it is possible to effectively remove the chemical emissions emitted from the image forming apparatus, by controlling an emission amount so that more negative ions are emitted which can effectively reduce the chemical emissions.

Advantageous Effects of Invention

According to the arrangement, the emission direction is changed in accordance with whether the image forming apparatus is in the operating state or the non-operating state. The arrangement allows the image forming apparatus to perform two functions of suppressing the effect of the exhaust gas of the image forming apparatus and purifying an indoor air.

Furthermore, more negative ions are emitted in the operating state than in the non-operating state. This makes it possible to reduce the effect of the exhaust gas more effectively.

This makes it possible to provide an image forming apparatus which can effectively suppress the effect of that exhaust gas containing a chemical emission which is emitted from the image forming apparatus, and which can purify an indoor air.

DESCRIPTION OF EMBODIMENTS

The following describes an embodiment of the present invention in detail.

Figure 2:
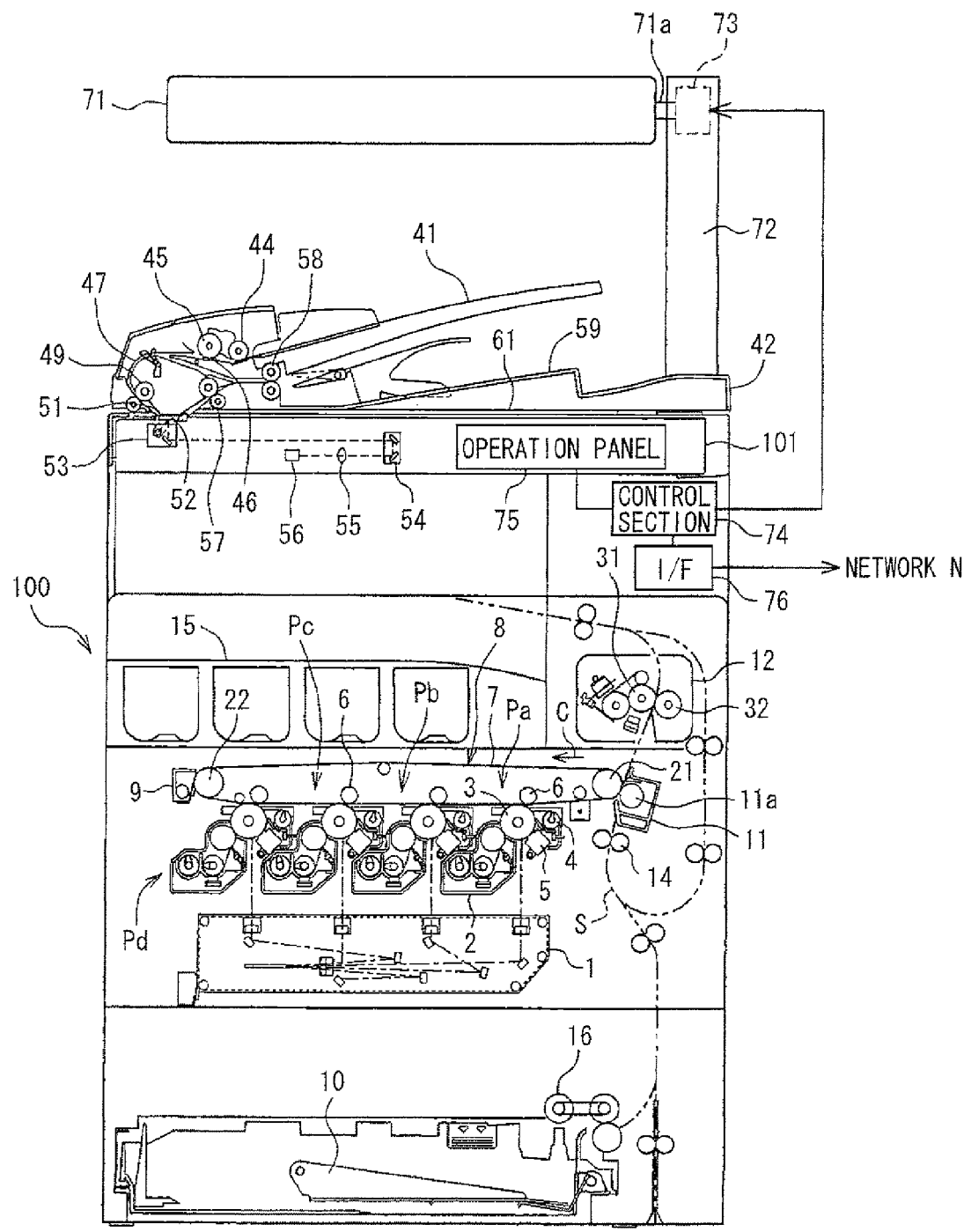
FIG. 2 is a cross-sectional view illustrating the one embodiment of the image forming apparatus of the present invention.

FIG. 2 is a cross-sectional view illustrating one embodiment of an image forming apparatus of the present invention. An image forming apparatus 100 records/forms a document image read by a document reading apparatus 101 or an externally-received image on a sheet of recording paper (recording material) in color or in monochrome.

The document reading apparatus 101 reads a document image which is carried by a document carrying section 42. In the document carrying section 42, upon setting of documents in a document set tray 41, a document pickup roller 44 is pressed against a surface of a document and rotated. Accordingly, the document is drawn out from the document set tray 41 and passed between a separating roller 45 and a separating pad 46. Thus, the document is separated from others so as to be carried to a carrying path 47.

In the carrying path 47, a head of the document makes contact with a document registration roller 49 so as to be aligned in parallel with the document registration roller 49. Then, the document is carried by the document registration roller 49, thereby being passed between a read guide 51 and a read glass 52. Further, the document is carried by a carrying roller 57 so as to be discharged to a paper output tray 59 via a paper output roller 58.

In the document reading apparatus 101, a surface of the document being passed between the read guide 51 and the read glass 52 is irradiated with light from a light source of a first scanning section 53 via the read glass 52. Light reflected by the surface of the document enters the first scanning section 53 via the read glass 52 so as to be reflected by a mirror of the first scanning section 53 and mirrors of a second scanning section 54, thereby being guided to an imaging lens 55. A document image is formed by the imaging lens 55 on a CCD (Charge Coupled Device) 56. The CCD 56 reads the document image and outputs image data indicative of the document image.

The document reading apparatus 101 also can read an image of a document placed on a scanner platen glass 61. The document carrying section 42 is pivotally supported on a back surface side of the document reading apparatus 101 so as to be openable and closable. When the document carrying section 42 is opened, the scanner platen glass 6 is exposed upward, thereby allowing placement of a document on the scanner platen glass 61. When the document carrying section 42 is closed after a document is placed on the scanner platen glass 61, the first scanning section 53 exposes a surface of the document placed on the scanner platen glass 61 while the first scanning section 53 and the second scanning section 54 are moved in a subscanning direction. Light reflected by the surface of the document is guided by the first scanning section 53 and the second scanning section 54 to the imaging lens 55. As a result, an image of the document is formed by the imaging lens 55 on the CCD 56. The first scanning section 53 and the second scanning section 54 are moved while a predetermined mutual speed relationship therebetween is maintained. This always maintains a positional relationship between the first scanning section 53 and the second scanning section 54 so that a length of an optical path does not change through which the light reflected by the surface of the document travels in the order of: first scanning section 53 and second scanning section 54→imaging lens 55→CCD 56. This allows the imaging lens 55 to always form a document image accurately on the CCD 56.

The whole document image read in this way is transmitted as image data to a laser exposure device 1 of the image forming apparatus 100. Accordingly, the image forming apparatus 100 records the document image on a sheet of recording paper.

The image forming apparatus 100 includes the laser exposure unit 1, four developing devices 2, four photoreceptor drums 3, four chargers 5, four cleaning devices 4, an intermediate transfer belt device 8, a fixing device 12, a paper carrying path S, a paper feeding tray 10, a paper output tray 15, etc.

Image data to be dealt with by the image forming apparatus 100 corresponds to a color image using the four colors of black (K), cyan (C), magenta (M), and yellow (Y), or to a monochrome image using a single color (e.g., black). The four developing devices 2, four photoreceptor drums 3, four chargers 5, and four cleaning devices 4 are provided so as to form respective four latent images corresponding respectively to the four colors. Thus, four image stations Pa, Pb, Pc, and Pd are formed so as to be associated with black, cyan, magenta, and yellow, respectively.

The four photoreceptor drums 3 are provided in substantially the center of the image forming apparatus 100.

Each of the four chargers 5 is charging means for uniformly charging a surface of a corresponding photoreceptor drum 3 to a predetermined electric potential. In addition to roller-type chargers and brush-type chargers, which are contact-type ones, noncontact-type ones can be used as the four chargers 5.

The laser exposure device 1 is a laser scanning unit (LSU) having a laser diode and reflecting mirrors. The laser exposure unit 1 exposes respective surfaces of the electrically-charged photoreceptor drums 3 in accordance with image data so as to form electrostatic latent images on the respective surfaces in accordance with the image data.

The developing devices 2 develop the electrostatic latent images formed on the photoreceptor drums 3 by using toner of the four colors (K, C, M, and Y). Each of the four cleaning devices 4 removes and collects toner which remains, after development and image transfer are carried out, on a surface of a corresponding photoreceptor drum 3.

The intermediate transfer belt device 8 provided above the four photoreceptor drums 3 includes an intermediate transfer belt 7, an intermediate transfer belt driving roller 21, a driven roller 22, four intermediate transfer rollers 6, and an intermediate transfer belt cleaning device 9.

The intermediate transfer belt driving roller 21, the four intermediate transfer rollers 6, the driven roller 22, etc. support the intermediate transfer belt 7 in a tensioned state, and rotates the intermediate transfer belt 7 in a direction indicated by an arrow C.

Each of the four intermediate transfer rollers 6 is rotatably supported in the vicinity of the intermediate transfer belt 7, and is pressed against a corresponding photoreceptor drum 3 via the intermediate transfer belt 7. A transfer bias for transferring a toner image formed on each of the photoreceptor drums 3 onto the intermediate transfer belt 7 is applied to a corresponding one of the four intermediate transfer rollers 6.

The intermediate transfer belt 7 is provided so as to have contact with the four photoreceptor drums 3. Four toner images formed respectively on the surfaces of the four photoreceptor drums 3 are superimposed one by one on the intermediate transfer belt 7, thereby forming a color toner image (toner image using the four colors). The intermediate transfer belt 7 is made in the form of an endless belt by use of a film having a thickness from approximately 100 μm to approximately 150 μm.

The four toner images formed respectively on the four photoreceptor drums 3 are transferred onto the intermediate transfer belt 7 by the four intermediate transfer rollers 6 which are pressed against a back surface of the intermediate transfer belt 7. A high-voltage transfer bias (a high voltage having a polarity (+) opposite to a polarity (−) of the electrically-charged toner) is applied to each of the four intermediate transfer rollers 6 so that the four intermediate transfer rollers 6 may transfer the four toner images formed respectively on the four photoreceptor drums 3 onto the intermediate transfer belt 7. Each of the four intermediate transfer rollers 6 is a roller made by using, as a base, a metal (e.g., stainless steel) shaft with a diameter from 8 to 10 mm and covering its surface with an electrically-conductive elastic material (e.g., EPDM, urethane foam, or the like). The electrically-conductive elastic material makes it possible to uniformly apply a high voltage to a sheet of recording paper.

As described above, the four toner images formed respectively on the surfaces of the four photoreceptor drums 3 are superimposed on the intermediate transfer belt 7 so that a color toner image indicated by image data is formed on the intermediate transfer belt 7. The intermediate transfer belt 7 and the color toner image formed thereon are carried, to a second transfer device 11 so that the color toner image may be transferred onto a sheet of recording paper by a transfer roller 11a in the second transfer device 11 which transfer roller 11a has contact with the intermediate transfer belt 7.

The intermediate transfer belt 7 and the transfer roller 11a of the second transfer device 11 are pressed against each other so as to form a fixing nip area. A voltage (a high voltage having the polarity (+) opposite to the polarity (−) of the electrically-charged toner) is applied to the transfer roller 11a of the second transfer device 11 so that the transfer roller 11a may transfer the color toner image formed on the intermediate transfer belt 7 onto a sheet of recording paper. In order that the fixing nip area is always secured, one of the transfer roller 11a of the second transfer device 11 and the intermediate transfer belt driving roller 21 is made from a hard material such as a metal while the other is made from a soft material such as an elastic roller (e.g., an elastic rubber roller, a foaming resin roller, or the like)

In some cases, the color toner image formed on the intermediate transfer belt 7 cannot be completely transferred by the second transfer device 11 onto a sheet of recording paper, and accordingly, toner remains on the intermediate transfer belt 7. The residual toner causes color mixture of toner in a next step. For this reason, the intermediate transfer belt cleaning device 9 removes and collects the residual toner. The intermediate transfer belt cleaning device 9 has, as a cleaning member, e.g., a cleaning blade for having contact with the intermediate transfer belt 7 so as to remove the residual toner. The back surface of the intermediate transfer belt 7 is supported by the driven roller 22 at a position where the cleaning blade has contact with an upper side of the intermediate transfer belt 7.

The paper feeding tray 10 is a tray for storing sheets of recording paper. The paper feeding tray 10 is provided below an image forming section of the image forming apparatus 100, and supplies to the image forming section the sheets of recording paper stored in the tray.

The image forming apparatus 100 has the paper carrying path S having a shape like "S" for carrying, to the paper output tray 15 via the second transfer device 11 and the fixing device 12, a sheet of recording paper supplied from the paper feeding tray 10. Provided along the paper carrying path S are a paper pickup roller 16, a paper registration roller 14, the fixing device 12, carrying rollers for carrying a sheet of recording paper, etc.

The paper pickup roller 16 is a suction roller which is provided on an end of the paper feeding tray 10 and which supplies sheets of recording paper one by one from the paper feeding tray 10 to the paper carrying path S. The carrying rollers are a plurality of small rollers for promoting and assisting carrying of a sheet of recording paper.

The paper registration roller 14 causes a carried sheet of recording paper to temporarily halt, aligns a head of the sheet of recording paper in parallel with the paper registration roller 14, and carries the sheet of recording paper in sync with rotation of the four photoreceptor drums 3 and the intermediate transfer belt 7 so that the color toner image formed on the intermediate transfer belt 7 is transferred onto the sheet of recording paper at the fixing nip area formed between the intermediate transfer belt 7 and the transfer roller 11a of the second transfer device 11.

For example, in accordance with a detection output of a pre-registration detection switch (not illustrated), the paper registration roller 14 carries the sheet of recording paper so that, at the fixing nip area formed between the intermediate transfer belt 7 and the transfer roller 11a of the second transfer device 11, a head of the color toner image formed on the intermediate transfer belt 7 matches with a head of an image forming area on the sheet of recording paper.

The fixing device 12 includes a heat roller 31, a pressure roller 32, etc. The heat roller 31 and the pressure roller 32 sandwich therebetween the sheet of recording paper passed through the fixing nip area formed between the intermediate transfer belt 7 and the transfer roller 11a of the second transfer device 11, thereby carrying the sheet of recording paper.

The heat roller 31 is controlled in accordance with a detection output of a temperature detector (not illustrated) so as to have a predetermined fixing temperature. The heat roller 31 and the pressure roller 32 apply heat and pressure onto the sheet of recording paper so that the toner image transferred onto the sheet of recording paper is melted, mixed, and pressed against the sheet of recording paper, thereby thermally fixing the toner image onto the sheet of recording paper.

The sheet of recording paper on which the color toner image is fixed is discharged by the carrying rollers onto the paper output tray 15 in such a manner that the sheet of recording paper faces down.

While performing printing on a sheet of recording paper by an electrophotographic printing method described above, the image forming apparatus 100 may generate a harmful exhaust gas containing chemical emissions such as a VOC and an odor. Main components of the exhaust gas are longifolene etc. which are presumed to be generated from a sheet of recording paper.

Lack of treatment of such a harmful exhaust gas is not preferable because a user of the image forming apparatus 100 suffers discomfort.

Figure 3:
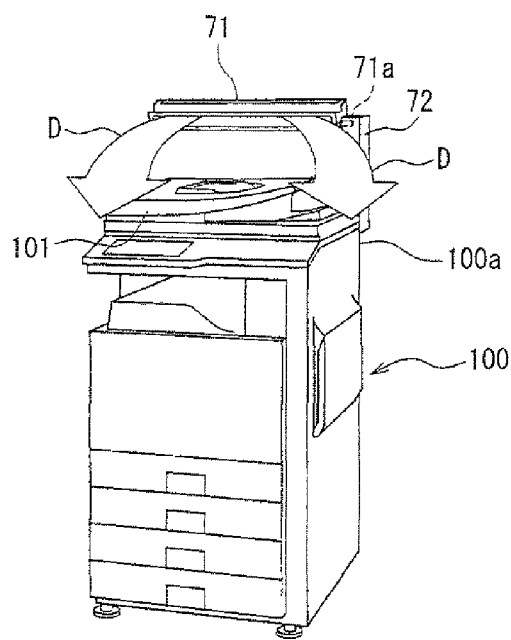
FIG. 3(a) and FIG. 3(b) are perspective views which illustrate two directions of ion emission from an ion generator of the image forming apparatus of FIG. 1.
Figure 3:
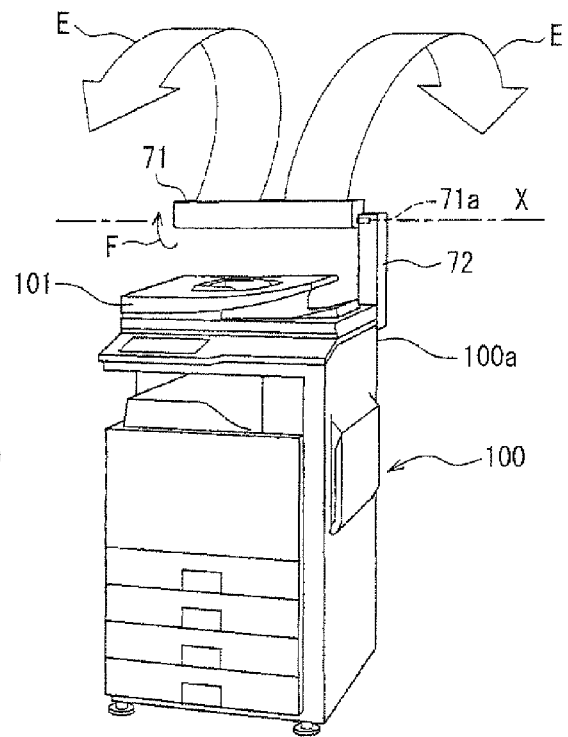

In view of this, as is illustrated in FIG. 2 and FIG. 3(a), the image forming apparatus 100 of the present embodiment includes an ion generator 71 above the main body of the image forming apparatus 100 so as to cause the ion generator 71 to generate positive ions and negative ions.

In the present embodiment, a plasmacluster ion generator is used as the ion generator 71, and positive ions and negative ions are emitted from the plasmacluster ion generator obliquely downward as is indicated by arrows D. Accordingly, the positive ions and negative ions cover, like an air curtain, mainly a front of the main body of the image forming apparatus 100, thereby removing the exhaust gas. It has been experimentally confirmed that such positive ions and negative ions can effectively suppress the effect of the exhaust gas even outside the image forming apparatus 100.

The exhaust gas is not generated when the image forming apparatus 100 is in a standby state. In this case, as illustrated in FIG. 3(b), the ion generator 71 changes an emission direction in which positive ions and negative ions are emitted from the ion generator 71 to an upward direction as indicated by arrows E. Accordingly, the ion generator 71 discharges and disperses positive ions and negative ions throughout a room, thereby removing floating bacteria in the air. Thus, the ion generator 71 purifies the air in a large space.

In the present embodiment, in the operating state of the image forming apparatus 100, the emission direction is set to an obliquely downward direction as is indicated by the arrows D in FIG. 3(a). However, the emission direction is not limited to the obliquely downward direction but can be changed to any direction, provided that positive ions and negative ions can be emitted toward the image forming apparatus 100. Further, in the standby state of the image forming apparatus 100, as illustrated in FIG. 3(b), the emission direction is set to the upward direction as is indicated by the arrows E. However, the emission direction is not limited to the upward direction but can be changed to any direction, provided that positive ions and negative ions can be emitted upward, i.e., provided that the positive ions and negative ions can be emitted within a range X which is a special range above alternate long and short dashed lines in FIG. 3(b).

As is evident from FIG. 2 and FIG. 3(a) and FIG. 3(b), a supporting column 72 is provided at a corner 100a on one lateral end of a back surface of the main body of the image forming apparatus 100 so as to be protruding upward. A shaft 71a of the ion generator 71 is supported at one end of the ion generator 71 by an upper end of the supporting column 72 so as to be rotatable in a direction indicated by an arrow F. The shaft 71a is connected with an output shaft of a motor driving unit 73. The motor driving unit 73 drives the shaft 71a to rotate back and forth, and consequently the ion generator 71 rotates back and forth in the direction indicated by the arrow F and in an opposite direction. Accordingly, the emission direction is changed to the direction indicated by the arrows D or the arrows E.

As illustrated in FIG. 2, the motor driving unit 73 is connected with a control section 74 (emission amount adjusting section and emission direction changing section) housed in the image forming apparatus 100. The motor driving unit 73 is driven under control of the control section 74. The control section 74 controls not only the motor driving unit 73 but also the image forming apparatus 100 as a whole. That is, the control section 74 controls driving of the motor driving unit 73 in accordance with a state of the image forming apparatus 100 (i.e., in accordance with whether the image forming apparatus 100 is in the operating state or in the non-operating state) so as to control a rotational position of the ion generator 71, thereby setting an emission direction to either the direction indicated by the arrows D or the direction indicated by the arrows E.

Furthermore, the control section 74 changes an ion emission amount of the ion generator 71 in accordance with a state of the image forming apparatus 100. Specifically, in a case where the image forming apparatus 100 is in the operating state, the control section 74 changes an emission amount ratio between positive ions and negative ions from that of a normal case (i.e., standby state) so that an emission amount of negative ions is increased. That is, negative ions are more effective for neutralization of an odor and removal of a VOC which are contained in the exhaust gas discharged from the fixing device 12 of the image forming apparatus 100 during a fixing process. In view of this, the normal emission amount ratio is switched to a ratio such that the emission amount of negative ions is increased while the exhaust gas is emitted from the image forming apparatus 100. This causes the ion generator 71 to discharge an airflow containing more negative ions toward the image forming apparatus 100. As a result, it is possible to effectively remove chemical emissions such as an odor and a VOC contained in the exhaust gas. Detailed control of this is described later.

The image forming apparatus 100 is arranged so that its back surface faces a wall or the like. In addition, the document carrying section 42 is pivotally supported, so as to be openable and closable, on a back surface side of the document reading apparatus 101, i.e., on a back surface side of the image forming apparatus 100. Accordingly, if the ion generator 71 is provided without discretion, e.g., at a position above the image forming apparatus 100 on its front side, the document carrying section 42 cannot be opened and closed properly.

In view of this, in the present embodiment, the supporting column 72 is provided at the corner 100a on one lateral end of the back surface of the main body, as illustrated in FIG. 2 and FIG. 3(a) and FIG. 3(b) and the ion generator 71 is horizontally supported at its one side by the supporting column 72. This makes it possible to free a space above the scanner platen glass 61 by opening the document carrying section 42 without being blocked by the ion generator 71. As a result, usability of the image forming apparatus 100 is not impaired. In addition, the ion generator 71 cannot be an obstacle even though the ion generator 71 is provided on the side of the back surface of the image forming apparatus 100 which back surface faces a wall surface. Therefore, providing the ion generator 71 outside the image forming apparatus 100 does not involve a problem of an increase in the installation space of the image forming apparatus 100.

Figure 4:
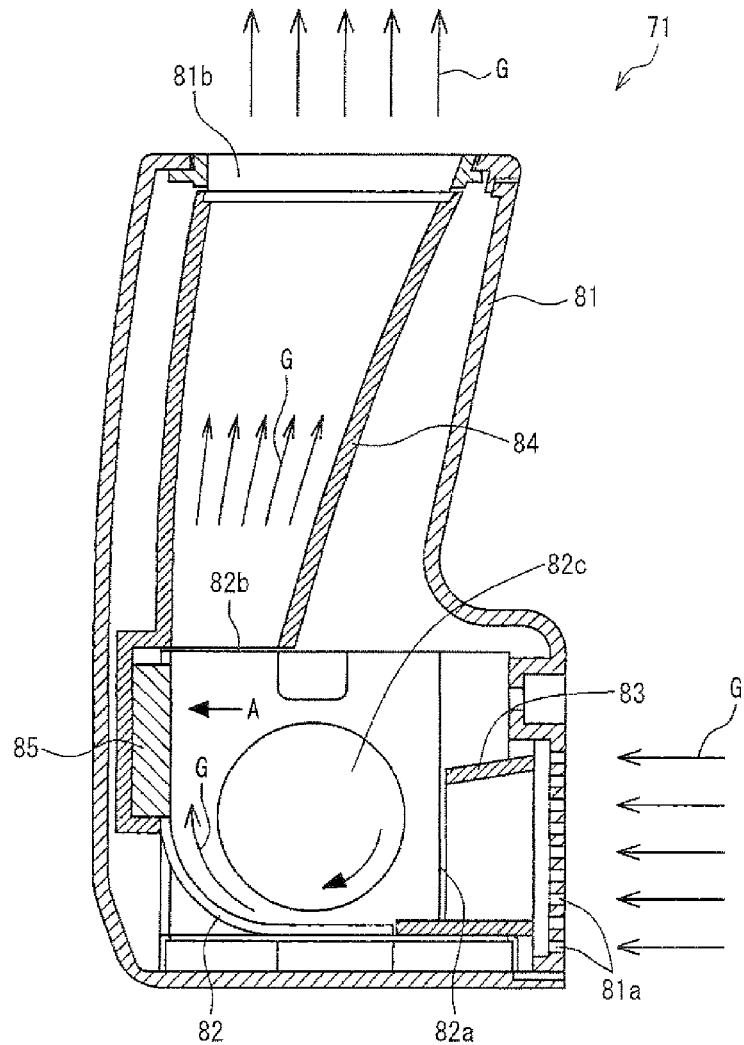
FIG. 4 is a cross-sectional view illustrating an ion generator of the image forming apparatus of FIG. 2.

FIG. 4 is a cross-sectional view illustrating the ion generator 71. The ion generator 71 includes a main body housing 81, a fan unit 82 provided to a lower part of the main body housing 81, a suction duct 83 provided between a plurality of suction openings 81a formed on a lower side wall of the main body housing 81 and a suction opening 82a of the fan unit 82, a blowout duct 84 provided between an upper blowout opening 81b formed on a top of the main body housing 81 and a blowout opening 82b of the fan unit 82, and a plurality of ion generating devices 85 provided so as to be adjacent to the fan unit 82.

The ion generator 71 has its longest dimension in parallel with a width direction of the image forming apparatus 100, as is illustrated in FIG. 2 and FIG. 3(a) and FIG. 3(b). Accordingly, the main body housing 81, the fan unit 82, the plurality of suction openings 81a, the suction duct 83, the blowout opening 82b, and the blowout duct 84 are also have respective longest dimensions in parallel with the width direction of the image forming apparatus 100. Further, the plurality of ion generating devices 85 are aligned in the width direction of the image forming apparatus 100.

A fan 82c of the fan unit 82 is driven by a motor (not illustrated) to rotate, thereby generating an airflow indicated by arrows G. Accordingly, the air is sucked in the fan unit 82 via the plurality of suction openings 81a and the suction duct 83 so that the air is supplied in the vicinity of the ion generating devices 85. Then, the air is discharged via the blowout duct 84 and the upper blowout opening 81b.

As is the case with the motor driving unit 73, the motor (not illustrated) of the fan 82c is also connected with the control section 74 housed in the image forming apparatus 100, and is driven under the control of the control section 74.

Figure 5:
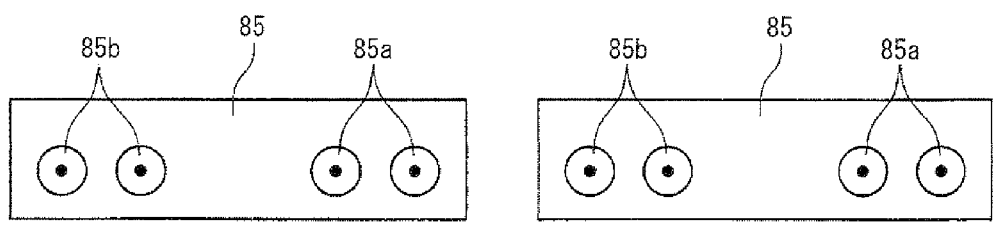
FIG. 5 is a plan view exemplifying ion generating devices of the ion generator of FIG. 4.

Each of the plurality of ion generating devices 85 is a Plasmacluster Ion® (PCI) generating device. When the plurality of ion generating devices 85 are viewed from a direction indicated by an arrow A in FIG. 4, two ion generating devices 85 are aligned in the width direction of the image forming apparatus 100, as is illustrated in FIG. 5. In each of the two ion generating devices 85, a pair of positive ion generating sections 85a for generating positive ions and a pair of negative ion generating sections 85b for generating negative ions are aligned in the width direction. As is the case with the motor driving unit 73, the plurality of ion generating devices 85 are also connected with the control section 74 housed in the image forming apparatus 100, and is driven under the control of the control section 74. That is, respective generation amounts of negative ions and positive ions are controlled by the control section 74. Such an ion generating device 85 is described in detail in Japanese Patent Application Publication, Tokukai, No. 2002-58731 A, which has been filed by the applicant of the present invention prior to the application of the present invention.

Positive ions and negative ions generated by the plurality of ion generating devices 85 and the airflow generated by the fan 82c of the fan unit 82 are discharged via the blowout duct 84 and the upper blowout opening 81b.

In this arrangement, as described above, the control section 74 in FIG. 2 takes overall control of the image forming apparatus 100. Upon turning-on of a power switch, the control section 74 controls driving of the sections of the image forming apparatus 100 by a predetermined procedure so as to place the image forming apparatus 100 in a standby state.

In the standby state, a user can instruct, via input operation of an operation panel 75, the image forming apparatus 100 to make copies of a document image. The control section 74 receives a print instruction signal for instructing the image forming apparatus 100 to make the copies in accordance with the input operation of the operation panel 75. Then, in response to the print instruction signal, the control section 74 starts operation of the image forming apparatus 100, places the image forming apparatus 100 in an operating state, reads the document image, and forms a copy of the document image on a sheet of recording paper. In this case, the image forming apparatus 100 serves as a copying machine.

The image forming apparatus 100 includes an interface 76 connected with a network. Accordingly, the image forming apparatus 100 is connected with an external terminal device (not illustrated) such as a personal computer via a network N so as to receive an image and a print instruction signal from the external terminal device via the interface 76. The control section 74 receives the image and the print instruction signal which have been received via the interface 76, starts the operation of the image forming apparatus 100 in response to the print instruction signal, places the image forming apparatus 100 in the operating state, and prints the image on a sheet of recording paper. In this case, the image forming apparatus 100 serves as a printer.

If a printing process is completed and a next printing process is not carried out for a predetermined time period, the image forming apparatus 100 enters the standby state again and waits for a next print instruction signal.

The standby state is referred to as a state in which a printing process is not carried, out but can be started immediately.

Figure 6:
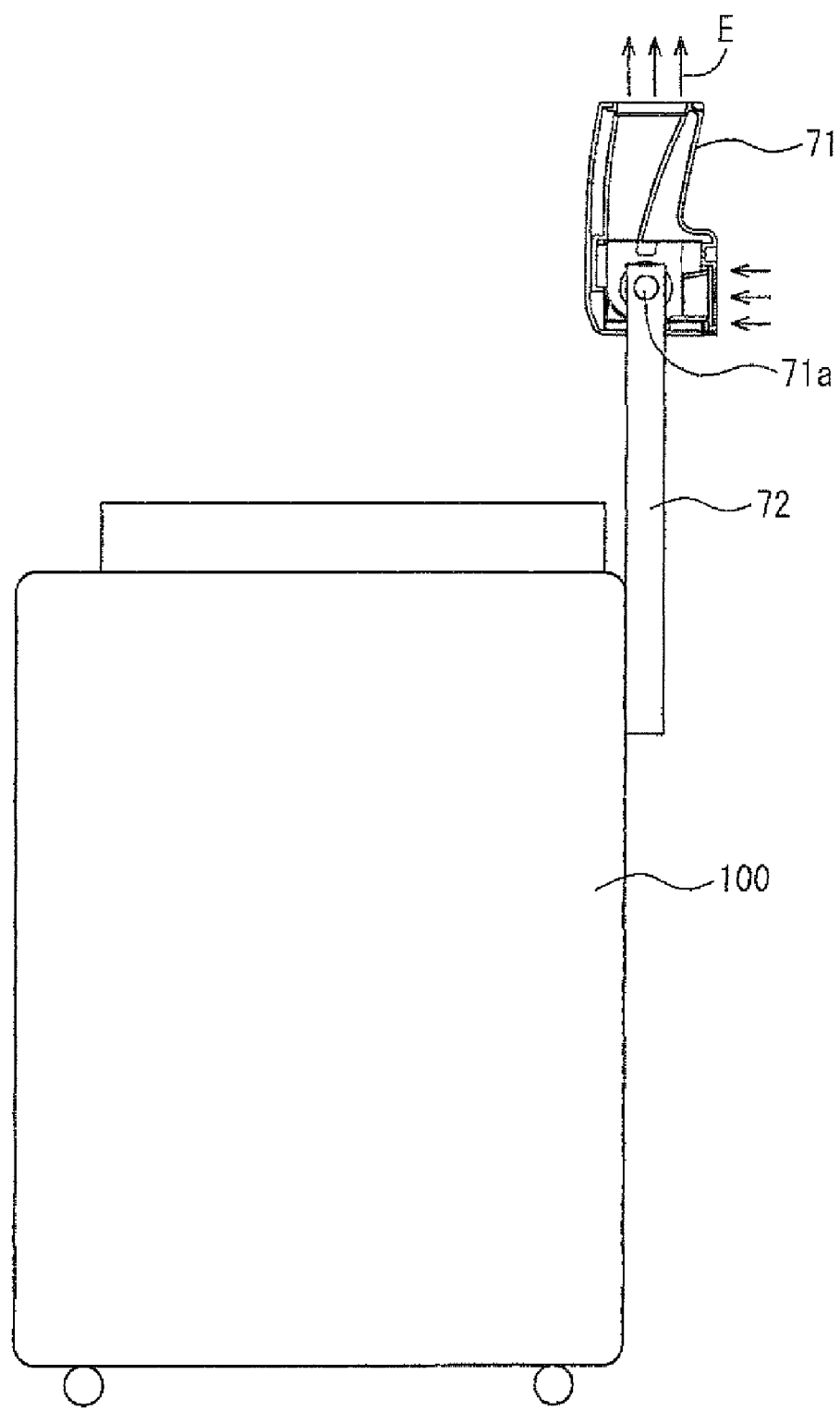
FIG. 6 is a side view illustrating a state in which a direction of ion emission from the ion generator of FIG. 4 of the image forming apparatus of FIG. 2 is set upward.

After placing the image forming apparatus 100 in the standby state, the control section 74 controls the driving of the motor driving unit 73 so as to control a rotation position of the ion generator 71, thereby setting an emission direction of ions from the ion generator 71 to the upward direction indicated by the arrows E as is illustrated in FIG. 3(b) and FIG. 6.

Accordingly, positive ions and negative ions flow and disperse throughout a room. As a result, floating bacteria in the air are removed by the positive ions and negative ions. The ion generator 71 purifies the air in a large space in this manner. In general, a set period of the standby state is longer than that of the operating state. Therefore, air purification is effectively carried out by flowing and dispersing positive ions and negative ions throughout a room during the standby state.

In the air purification, the control section 74 may control the driving of the motor driving unit 73 so as to rotate the ion generator 71 back and forth within a predetermined angular range around the shaft 71a. In other words, the ion generating device 71 is caused to swing back and forth. This makes it possible to expand an emission range of positive ions and negative ions.

Alternatively, the control section 74 controls the driving of the motor of the fan 82c so as to increase a rotation speed of the fan 82c of the fan unit 82. This increases an emission speed and an emission amount of the air to be discharged from the ion generator 71, thereby further expanding the emission range of positive ions and negative ions.

Figure 7:
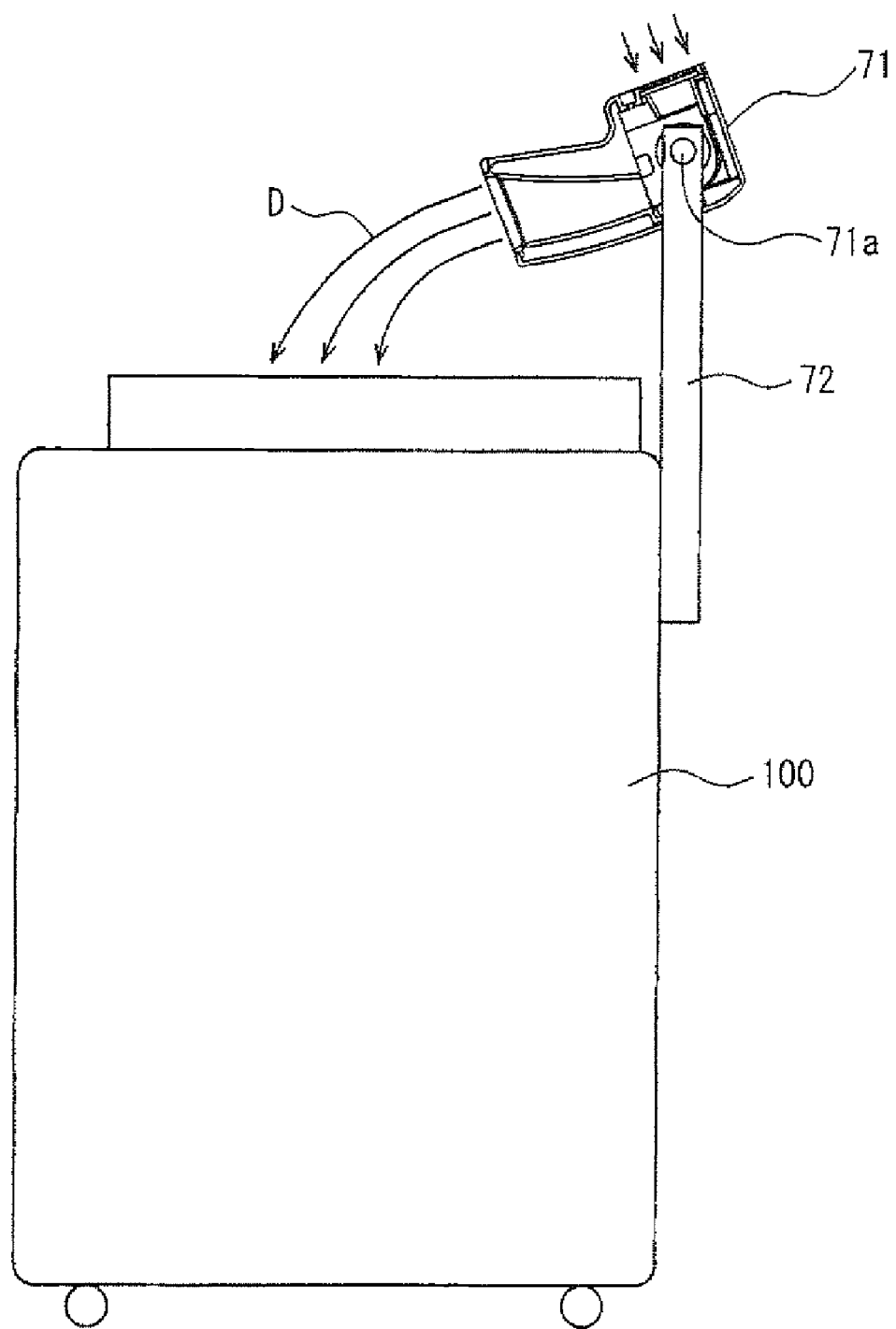
FIG. 7 is a side view illustrating a state in which a direction of ion emission from the ion generator of FIG. 4 of the image forming apparatus of FIG. 2 is set obliquely downward.

After placing the image forming apparatus 100 in the operating state, the control section 74 controls the driving of the motor driving unit 73 so as to control a rotation position of the ion generator 71, thereby setting an emission direction of ions from the ion generator 71 to the obliquely downward direction indicated by the arrows D as is illustrated in FIG. 3(a) and FIG. 7.

Accordingly, positive ions and negative ions cover mainly the front of the main body of the image forming apparatus 100, thereby removing the chemical emissions (a VOC and an odor) contained in the exhaust gas. Usually, a user stands in front of the main body of the image forming apparatus 100. Accordingly, when positive ions and negative ions are emitted in the direction indicated by the arrows D so that positive ions and negative ions cover mainly the front of the main body, it is possible to effectively remove the chemical emissions contained in the exhaust gas in the vicinity of the user.

Also in this case, the control section 74 may control the driving of the motor driving unit 73 so as to cause the ion generator 71 to rotate back and forth, i.e., swing back and forth, within the predetermined angular range around the shaft 71a.

Alternatively, the control section 74 controls the driving of the motor of the fan 82c of the fan unit 82 so as to decrease a rotation speed of the fan 82c. This causes the ion generator 71 to mildly discharge the air. Accordingly, the airflow gradually curves downward as is indicated the arrows D. This prevents the air from strongly impinging on a user standing in front of the main body of the image forming apparatus 100. As a result, it is possible to mildly disperse positive ions and negative ions, and cause the positive ions and negative ions to surely cover the front of the main body of the image forming apparatus 100.

According to the present embodiment, furthermore, after placing the image forming apparatus 100 in the operating state, the control section 74 controls driving of the ion generating devices 85 so that a generation ratio between positive ions and negative ions is changed from that of the normal case, thereby generating more negative ions than those of the normal case. In this case, it is preferable that an electric power required for generating positive ions be used as an electric power for generating negative ions so that only the negative ions are generated. If an extra electric power is available, positive ions may be also generated together.

This increases an emission amount of negative ions from the ion generator 71. As a result, it is possible to remove more effectively the chemical emissions (a VOC and an odor) contained in the exhaust gas discharged from the image forming apparatus 100.

In addition to increasing the generation amount of negative ions, the control section 74 may control the driving of the motor of the fan 82c of the fan unit 82 so as to increase a rotation speed of the fan 82c. This makes it possible to increase more effectively an emission speed at which the ion generator 71 emits the air and an emission amount of the air.

Figure 1:
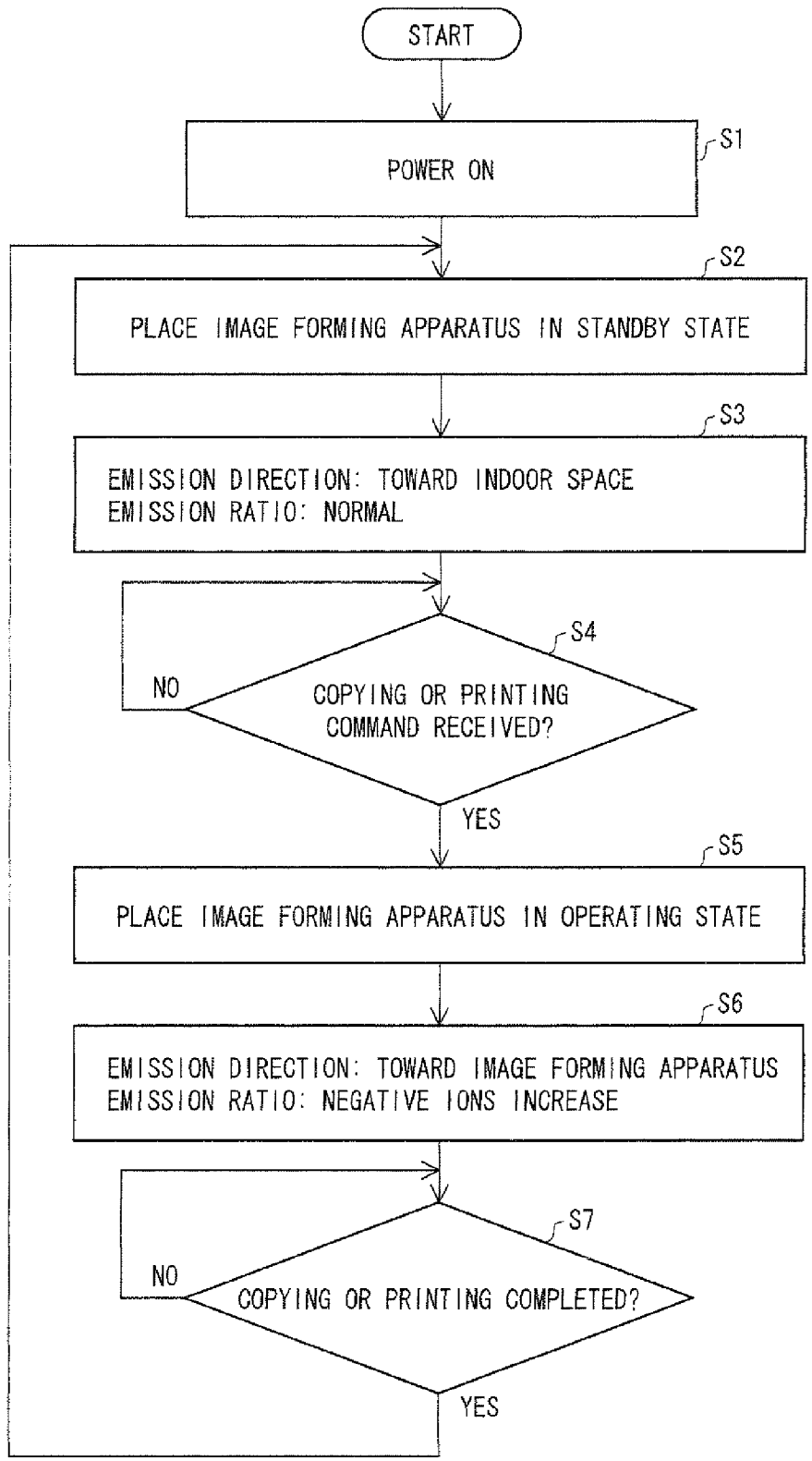
FIG. 1 is a flowchart of one embodiment of an image forming apparatus of the present invention, which flowchart illustrates control processes of switching between two operations of an ion generator in accordance with a state of the image forming apparatus.

FIG. 1 shows a control flow for switching between the two emission directions and switching between the two emission amount ratios in accordance with a state of the image forming apparatus 100.

Upon turning-on of the power switch of the image forming apparatus 100 (S1), the control section 74 places the image forming apparatus 100 in the standby state (S2). After placing the image forming apparatus 100 in the standby state, the control section 47 sets an emission direction to the upward direction so that the ion generator 71 may emit positive ions and negative ions into an indoor space at a predetermined ratio (at a normal ratio) (S3).

Then, upon receipt of a copying instruction from the operation panel 75, or upon receipt of a print instruction signal (S4), the control section 74 places the image forming apparatus 100 in the operating state (S5). After placing the image forming apparatus 100 in the operating state, the control section 74 switches the emission direction from the upward direction to the obliquely downward direction so that positive ions and negative ions are emitted toward the image forming apparatus 100. At the same time, the control section 74 switches the emission ratio from the normal ratio to another ratio so that more negative ions are emitted (S6).

Then, the control section 74 confirms completion of a copying or printing process, on the basis of, e.g., a predetermine time passage from a discharge of a last sheet of recording paper (S7). Then, the control section 74 returns to S2 to place the image forming apparatus 100 in the standby state again. Then, in S3, the control section 74 restores the original emission direction (i.e., the upward direction) and the original emission amount ratio (i.e., the normal ratio) so that the ion generator 71 may emit positive ions and negative ions into the indoor space at the predetermined emission amount ratio.

As described above, in the present embodiment, a direction of the ion generator 71 is controlled in accordance with whether the image forming apparatus 100 is in the standby state or the operating state, thereby switching between the two emission directions. This makes it possible to purify the air in the standby state and remove, in the operating state, the chemical emissions such as an odor and a VOC contained in the exhaust gas. That is, the arrangement allows one ion generator 71 to perform two functions.

Furthermore, selected during the operating state is the generation ratio between positive ions and negative ions which is different from that of the normal case. This causes the ion generator 71 to generate more negative ions than those of the normal case. As a result, more negative ions are emitted toward the image forming apparatus 100. This allows more effective removal of the chemical emissions (a VOC and an odor) contained in the exhaust gas discharged from the image forming apparatus 100. The present embodiment combines an arrangement in which more negative ions are emitted during the operating state with an arrangement in which an emission direction of ions is switched between the two directions in accordance with a state of operation of the image forming apparatus 100. However, this combination is not essential. For example, an emission direction can be manually switched, provided that an ion emitting device is externally attached to the image forming apparatus 100, and the ion emitting device can emit ions toward the image forming apparatus 100.

It has been experimentally confirmed that the effect of the exhaust gas of the image forming apparatus 100 can be effectively suppressed by covering with ions, like an air curtain, the image forming apparatus 100. This allows provision of the ion generator 71 outside the image forming apparatus 100. As a result, it is possible to prevent an increase in the size of the main body of the image forming apparatus 100. In addition, since the ion generator 71 purifies an indoor air, there is no need for an additional air purifier. As a result, it is possible to effectively use an indoor space and reduce cost of equipment.

Figure 8:
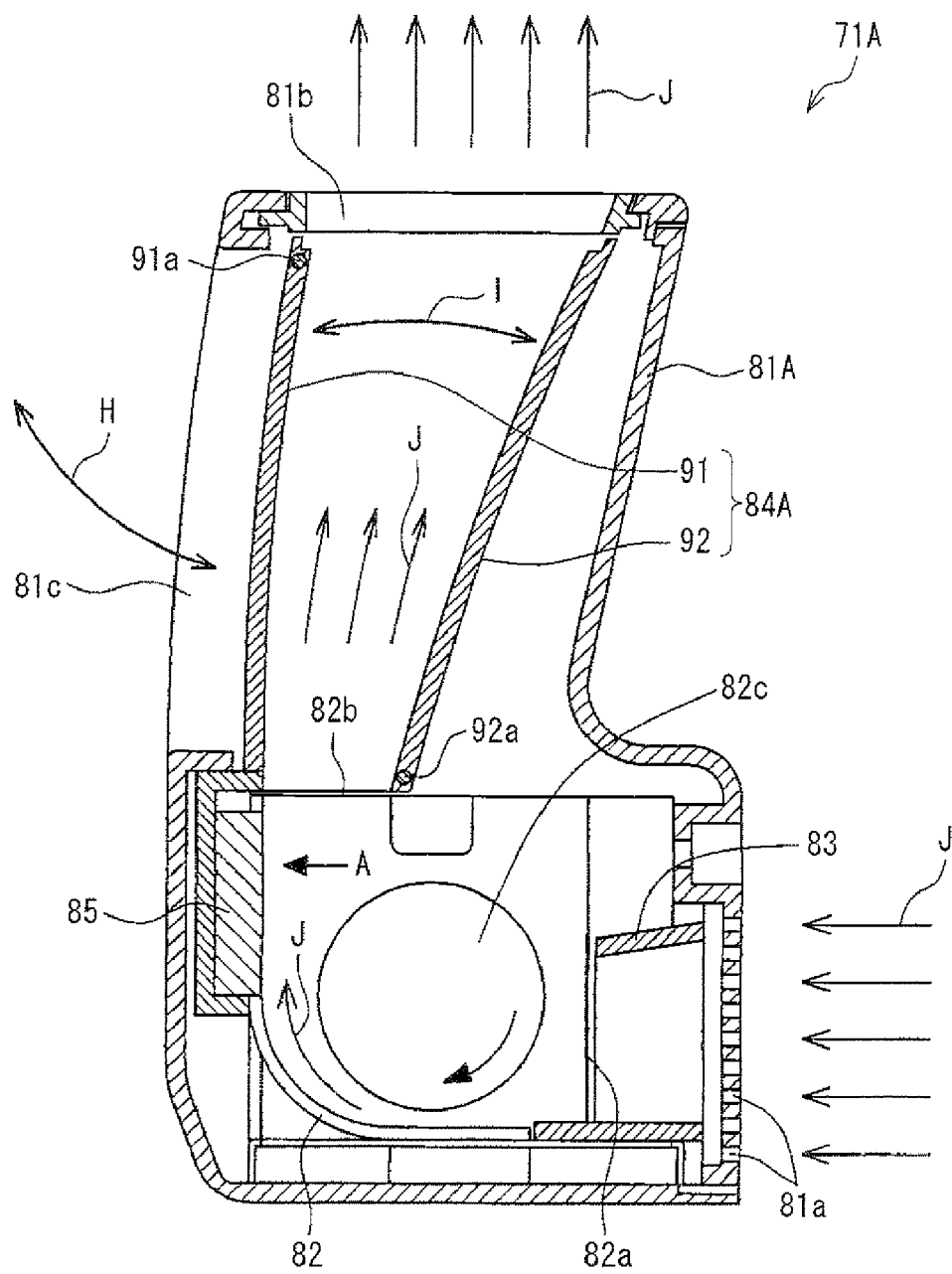
FIG. 8 is a cross-sectional view illustrating another example of an ion generator of the image forming apparatus of FIG. 2.

FIG. 8 is a cross-sectional view illustrating another example of the ion generator. Parts illustrated in FIG. 8 which function in the same way as those illustrated in FIG. 4 are given the same reference numerals, and explanations of such parts are omitted.

As illustrated in FIG. 8, instead of the main body housing 81 and the blowout duct 84 which are illustrated in FIG. 4, a main body housing 81A and a blowout duct 84A are provided to an ion generator 71A.

The main body housing 81A has not only a plurality of suction openings 81a and an upper blowout opening 81b as is the case with the main body housing 81 in FIG. 4, but also a side blowout opening 81c.

The blowout duct 84A has a first movable duct wall 91 and a second movable duct wall 91 which face each other. The first movable duct wall 91 is pivotally supported via a shaft 91a provided at an upper end of the first movable duct wall. Accordingly, the first movable duct wall 91 can be turned back and forth around the shaft 91a in directions indicated by an arrow H. The second movable duct wall 92 is pivotally supported via a shaft 92a provided at a lower end of the second movable duct wall 92. Accordingly, the second movable duct wall 92 can be turned back and forth around the shaft 92a in directions indicated by an arrow I.

Respective shafts 91a and 92a of the first movable duct wall 91 and the second movable duct wall 92 are driven at a time to rotate back and forth at a time by a motor driving unit (not illustrated) for the duct.

The control section 74 in the image forming apparatus 100 controls driving of the motor driving unit for the duct in accordance with whether the image forming apparatus 100 is in the standby state or the operating state, thereby rotating the shafts 91a and 92a back and forth at a time. As a result, the first movable duct wall 91 and the second movable duct wall 92 are selectively positioned as is illustrated in FIG. 8 or 9.

In a case where the first movable duct wall 91 and the second movable duct wall 92 are positioned as is illustrated in FIG. 8, the first movable duct wall 91 closes the side blowout opening 81c. Accordingly, in the ion generator 71A, an airflow is generated in a direction indicated by arrows J, and flows through the following route: suction openings 81a→suction duct 83→neighborhood of ion generating devices 85 in fan unit 82→blowout opening 82b→blowout duct 84A→upper blowout opening 81b, finally being discharged upward.

Figure 9:
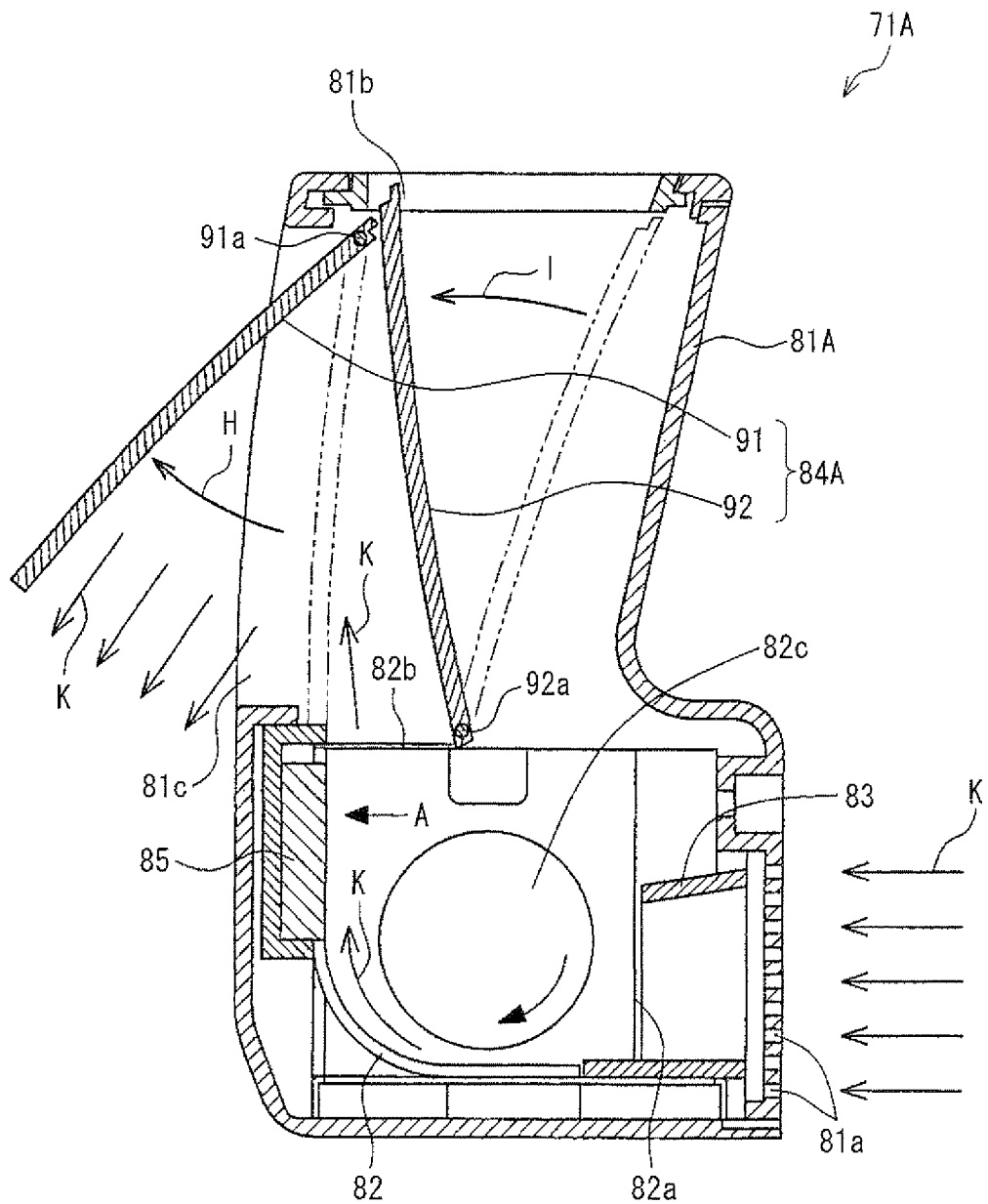
FIG. 9 is a side view illustrating a state in which a direction of ion emission from the ion generator of FIG. 8 is set obliquely downward.

In a case where the first movable duct wall 91 and the second movable duct wall 92 are positioned as is illustrated in FIG. 9, the first movable duct wall 91 opens the side blowout opening 81c, and the second movable duct wall 92 closes the upper blowout opening 81b. Accordingly, in the ion generator 71A, an airflow is generated in a direction indicated by arrows K, and flows through the following route: suction openings 81a→suction duct 83→neighborhood of ion generating devices 85 in fan unit 82→blowout opening 82b→side blowout opening 81c, finally being discharged obliquely downward.

Figure 10:
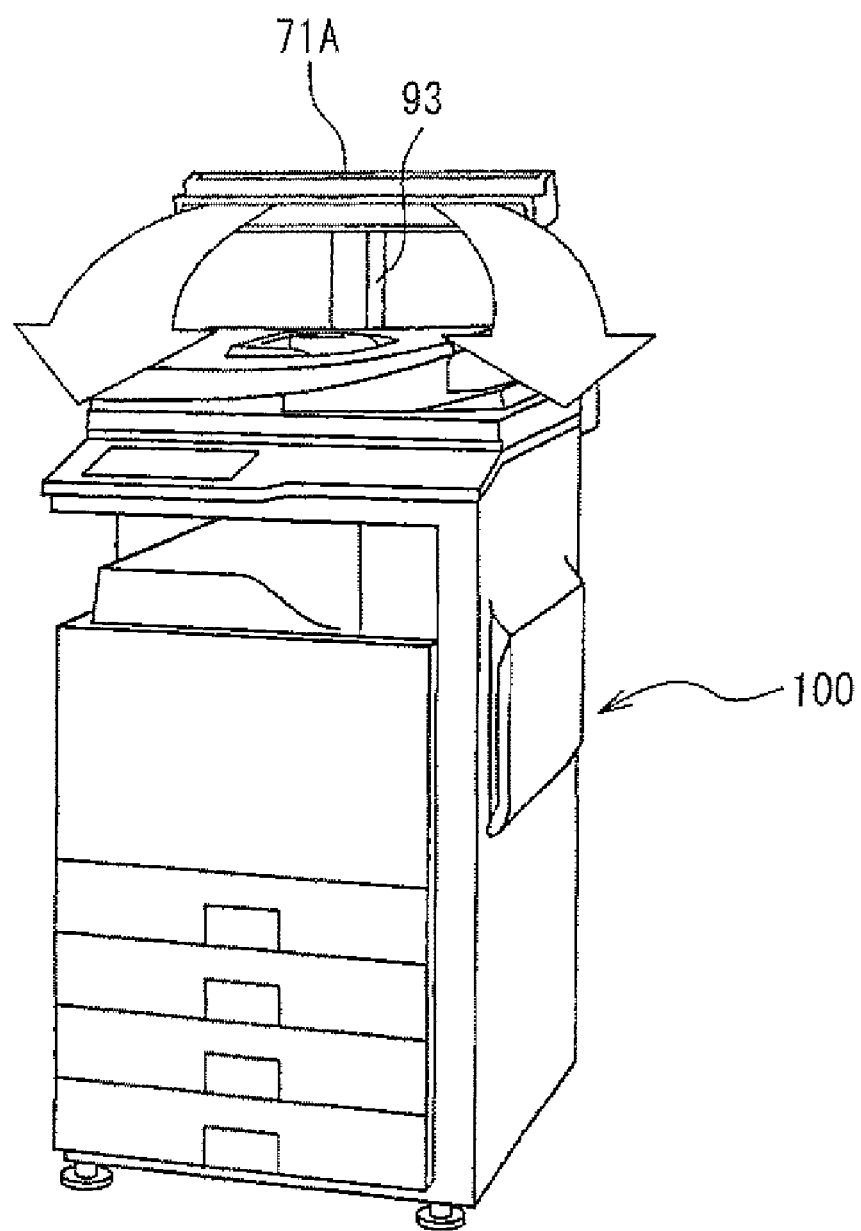
FIG. 10 is a perspective view illustrating a supporting structure which supports the ion generator of FIG. 8 of the image forming apparatus of FIG. 2.

FIG. 10 illustrates the image forming apparatus 100 and the ion generator 71A attached thereto. A supporting column 93 is provided so as to be protruding upward on a centerline of the back surface of the main body of the image forming apparatus 100. The ion generator 71A is stably supported at its center by an upper end of the supporting column 93.

Figure 11:
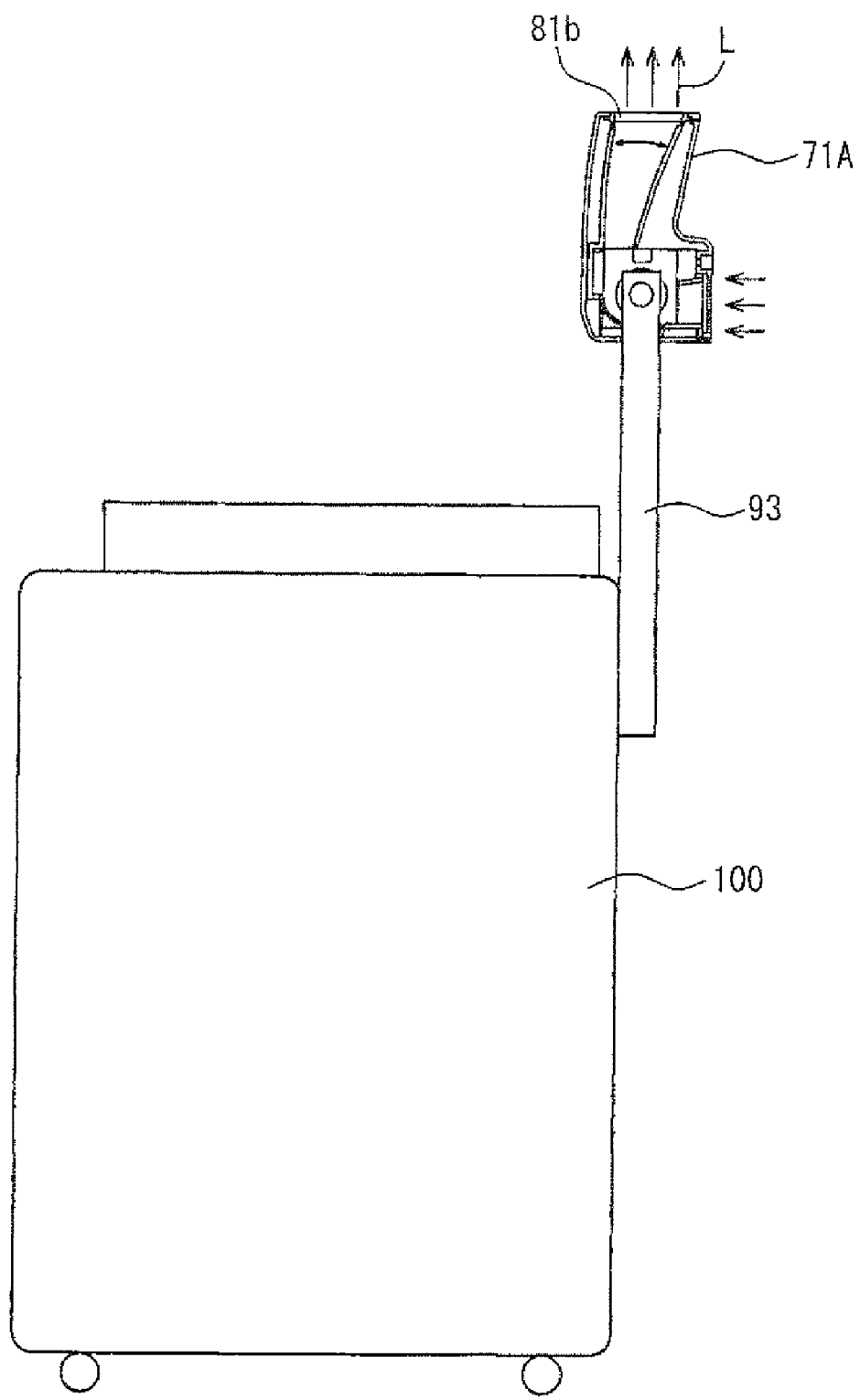
FIG. 11 is a side view illustrating a state in which a direction of ion emission from the ion generator of FIG. 8 of the image forming apparatus of FIG. 2 is set upward.

After placing the image forming apparatus 100 in the standby state, the control section 74 controls the driving of the motor driving unit for the duct so as to rotate the shafts 91a and 92a at a time, thereby positioning the first movable duct wall 91 and the second movable duet wall 92 as is illustrated in FIG. 8. Accordingly, as illustrated in FIG. 11, the air, and positive ions and negative ions are discharged from the upper blowout opening 81b of the ion generator 71 in an upper direction indicated by arrows L. As a result, the positive ions and negative ions flow and disperse throughout a room, thereby effectively purifying the air.

In the air purification, an emission range of the positive and negative ions can be further expanded in such a manner that driving of the motor of the fan 82c is controlled so that a rotation speed of the fan 82c is increased, thereby increasing an emission speed and an emission amount of the air to be discharged from the ion generator 71.

Figure 12:
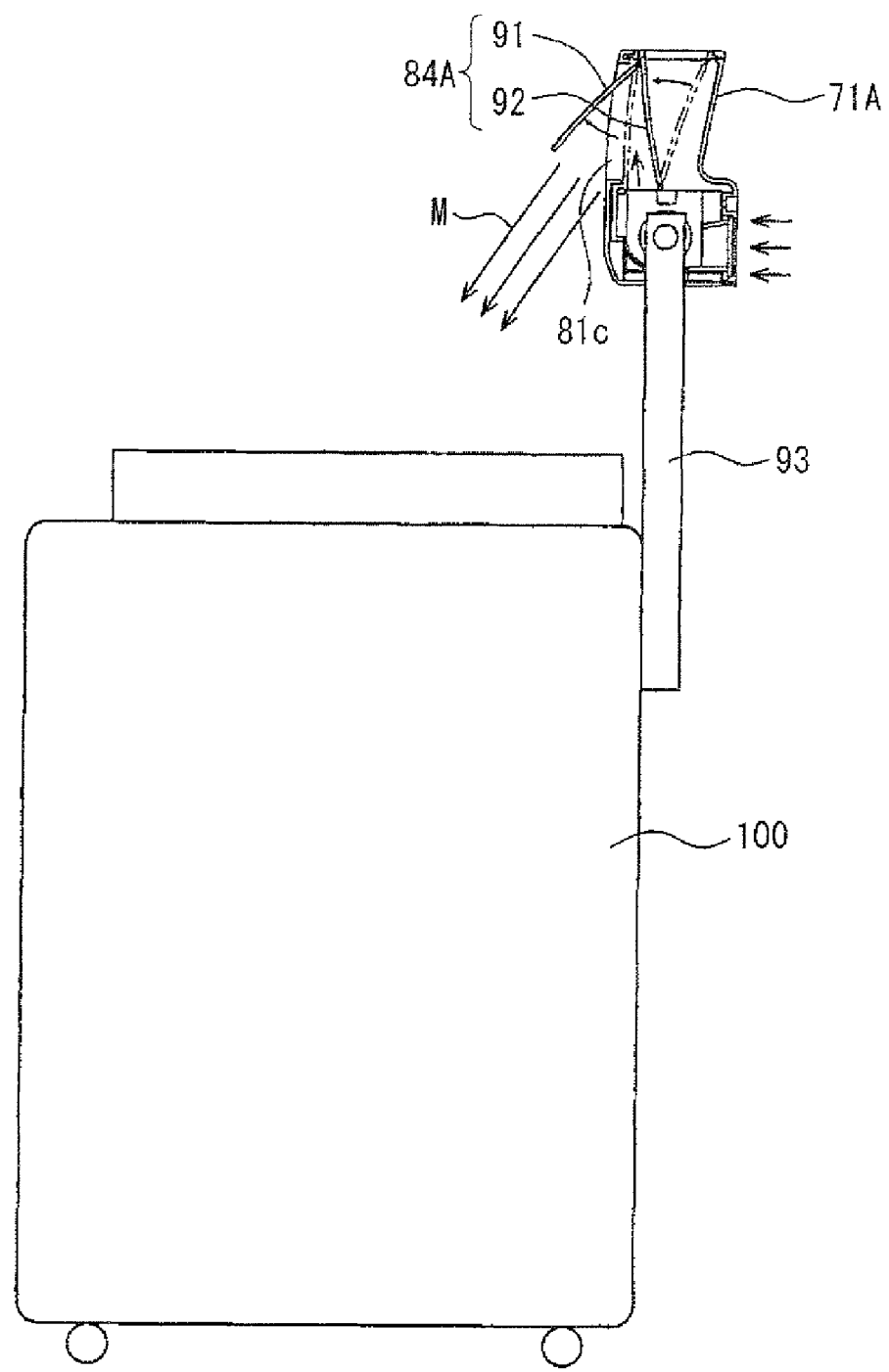
FIG. 12 is a side view illustrating a state in which a direction of ion emission from the ion generator of FIG. 8 of the image forming apparatus of FIG. 2 is set obliquely downward.

After placing the image forming apparatus 100 in the operating state, the control section 74 controls the driving of the motor driving unit for the duct so as to rotate the shafts 91a and 92a at a time, thereby positioning the first movable duct wall 91 and the second movable duct wall 92 as is illustrated in FIG. 9. Accordingly, as illustrated in FIG. 12, the air, and positive ions and negative ions are discharged from the side blowout opening 81c of the ion generator 71 in an obliquely downward direction indicated by arrows M. The positive ions and negative ions cover mainly the front of the main body of the image forming apparatus 100, thereby effectively removing an odor of the exhaust gas in the vicinity of a user.

In this case, in order that the front of the main body of the image forming apparatus 100 is surely covered by the positive ions and negative ions, the driving of the motor of the fan 82c can be controlled so that a rotation speed of the fan 82c is decreased, thereby dispersing the positive ions and negative ions mildly.

Thus, the use of the ion generator 71A also makes it possible to purify the air in the standby state and remove an odor of the exhaust gas in the operating state, by switching between the two emission directions in accordance with whether the image forming apparatus 100 is in the standby state or the operating state.

The above has described a preferable embodiment of the present invention with reference to figures. However, needless to say, the present invention is not limited to the above. It will be obvious that a person skilled in the art can arrive at various modifications and alternations within the scope of the following claims. Such modifications and alternations are naturally encompassed in the technical scope of the present invention.

For example, with regard to the operating state and the standby state of the image forming apparatus, which are dealt with in the present embodiment, power-saving control may be performed as below. In a case where the image forming apparatus is in a non-operating state for a long period, the standby state is switched to a power-saving state in which power consumption is small, and is further switched to a sleep state in which power consumption is much smaller. Upon receipt of a print instruction, the image forming apparatus returns to the operating state. Also in the power-saving state and the sleep state, no exhaust gas is generated as well as in the standby state. Therefore, an emission direction can be the upward direction so that positive ions and negative ions continue to be emitted upward. Particularly, the image forming apparatus is placed in the sleep state at nighttime or the like. Therefore, the ion generator can sufficiently purify an indoor air while nobody is in the room, by continuing to emit positive ions and negative ions upward. In the present Description, the operating state of the image forming apparatus refers to a state in which the image forming apparatus carries out print processing, and the non-operating state of the image forming apparatus refers to a state in which the power of the image forming apparatus is ON and in which the image forming apparatus does not carry out print processing. The non-operating state includes the standby state, the power-saving state, and the sleep state.

It may be arranged such that the ion generator 71 and the motor driving unit 73 can be optionally attached to the image forming apparatus. In this case, a control section for controlling the driving of the motor driving unit 73 etc. is provided on a side of the ion generator 71. The control section and the control section 74 of the image forming apparatus 100 are connected via a serial cable and receptacles. The control section 74 of the image forming apparatus 100 transmits instructions to the control section on the ion generator 71 side via data communications between the two control sections so as to cause the control section on the ion generator 71 side to control the motor driving unit 73 etc.

Furthermore, an installation position of the ion generator 71 can be changed in accordance with a structure and a usage pattern of the image forming apparatus. In the present embodiment, the supporting column is provided so as to be protruding on the back surface side of the image forming apparatus, and the ion generator 71 is horizontally held by the upper end of the supporting column, on the assumption that the image forming apparatus is installed so that its back surface faces a wall or the like. However, depending on a structure and a usage pattern of the image forming apparatus, the image forming apparatus may be installed so that its side surface faces a wall or the like. In this case, the supporting column is provided on the side surface of the image forming apparatus, and the ion generator 71 is held by the upper end of the supporting column. Accordingly, the ion generator 71 is provided in the vicinity of the wall. As a result, the ion generator 71 cannot be an obstruction. Instead of using the supporting column, the ion generator 71 can be vertically attached to the image forming apparatus, or can be directly attached to an outer surface of the main body of the image forming apparatus. Furthermore, a plurality of ion generators 71 can be attached to the image forming apparatus in a distributed manner.

As described above, an image forming apparatus of the present invention is an image forming apparatus for forming an image on a recording material, including: an ion generator, provided outside a main body of the image forming apparatus, for generating and emitting positive ions and negative ions; an emission direction changing section for changing, in accordance with whether the image forming apparatus is in an operating state or a non-operating state, a direction of ion emission from the ion generator; and an emission amount adjusting section for changing, in accordance with whether the image forming apparatus is in the operating state or the non-operating state, a ratio between positive ions and negative ions to be emitted from the ion generator so that more negative ions are emitted in the operating state than in the non-operating state.

According to the arrangement, the emission direction changing section changes the emission direction in accordance with whether the image forming apparatus is in the operating state or the non-operating state. In the operating state of the image forming apparatus, an exhaust gas is generated. Accordingly, it is preferable to set an emission direction to the one in which an odor of the exhaust gas is effectively neutralized. In the non-operating state of the image forming apparatus, no exhaust gas is generated. Accordingly, it is preferable to set an emission direction to the one in which floating bacteria in the air are effectively removed. That is, the arrangement allows the image forming apparatus to perform two functions of suppressing the effect of the exhaust gas of the image forming apparatus and purifying an indoor air.

In addition, according to the arrangement, ion generator is provided outside the main body of the image forming apparatus. This makes it possible to prevent an increase in the size of the main body, and eliminate the need for an additional air purifier. As a result, an indoor space can be effectively used.

For example, positive ions and negative ions are generated and emitted by the ion generator at a time. Such positive ions and negative ions are preferable for the present invention because they can effectively remove floating bacteria in the air and can effectively neutralize an odor of the exhaust gas of the image forming apparatus.

Furthermore, according to the arrangement, the emission amount adjusting section changes, in accordance with whether the image forming apparatus is in the operating state or the non-operating state, a ratio between positive ions and negative ions to be emitted from the ion generator so that more negative ions are emitted in the operating state than in the non-operating state. In the operating state, an exhaust gas containing chemical emissions such as a VOC and an odor is generated. Accordingly, it is possible to effectively remove the chemical emissions emitted from the image forming apparatus, by controlling an emission amount so that more negative ions are emitted which can effectively reduce the chemical emissions.

In the present invention, further, the image forming apparatus includes the emission direction changing section which changes an emission direction in accordance with whether the image forming apparatus is in the operating state or the non-operating state. The emission direction changing section may be arranged such that while the image forming apparatus is in the operating state, the emission direction changing section sets the direction of ion emission from the ion generator to a direction toward the image forming apparatus; and while the image forming apparatus is in the non-operating state, the emission direction changing section sets the direction of ion emission from the ion generator to a direction opposite to the direction toward the image forming apparatus.

According to the arrangement, the emission direction changing section switches the two emission directions in accordance with whether the image forming apparatus is in the operating state or the non-operating state. Accordingly, in the operating state, positive ions and negative ions are intensively emitted toward the image forming apparatus while, in the non-operating state, positive ions and negative ions are emitted in the direction opposite to the direction toward the image forming apparatus, i.e., emitted into an indoor space. This allows a single image forming apparatus to perform the two functions more effectively.

In the present invention, further, the emission amount adjusting section can be arranged such that the emission amount adjusting section causes the ion generator to emit negative ions while the image forming apparatus is in the operating state, and the emission amount adjusting section causes the ion generator to emit negative ions and positive ions while the image forming apparatus is in the non-operating state.

According to the arrangement, in the operating state, negative ions are emitted toward the image forming apparatus so that chemical emissions contained in the generated exhaust gas are effectively removed. On the other hand, no exhaust gas is generated in the non-operating state. Accordingly, negative ions and positive ions are widely dispersed in the direction opposite to the direction toward the image forming apparatus, i.e., into an indoor space so that mold funguses etc. floating in the indoor space are reduced.

In the present invention, the emission amount adjusting section can be arranged such that, in response to an operation of a copy start key, or, upon reception of a print request, the emission amount adjusting section increases an amount of negative ions to be emitted by the ion generator.

In a case where the copy start key is operated, or a print request is received, the image forming apparatus enters the operating state. This arrangement allows the image forming apparatus to properly select either the operating state or the non-operating state.

Further, the ion generator is preferably attached to the image forming apparatus via a supporting member in such a manner that the ion generator is positioned above the image forming apparatus.

According to the arrangement, the ion generator is supported by the supporting member which is provided to the image forming apparatus so as to be protruding upward. Accordingly, the ion generator is provided above the image forming apparatus. As a result, an installation space for the image forming apparatus does not increase. Emitting positive ions and negative ions downward, i.e., toward the image forming apparatus makes it possible to easily cover the image forming apparatus. As a result, the positive ions and negative ions can surely suppress the effect of the exhaust gas.

The supporting member is preferably provided so as to be protruding upward at one corner section on a back surface side of the image forming apparatus and so as to support one end of the ion generator.

The arrangement frees a space above the image forming apparatus. As a result, usability of the image forming apparatus is not impaired.

The supporting member is preferably provided so as to be protruding upward on a centerline of the back surface of the image forming apparatus, and preferably supports the ion generator at a central position of the ion generator.

According to the arrangement, the ion generator is stably supported by the image forming apparatus.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Industrial Applicability

The present invention is applicable to various image forming apparatuses involving generation of a chemical emission.

Reference Signs List 71 and 71A Ion generator
72 and 93 Supporting column (supporting member)
73 Motor driving unit
74 Control section (Emission amount adjusting section and emission direction changing section)
81 Main body housing
82 Fan unit
83 Suction duct
84 and 84A Blowout duct
85 Ion generating device

The invention claimed is:

1. An image forming apparatus for forming an image on a recording material, comprising:
  an ion generator, provided outside a main body of the image forming apparatus, for generating and emitting positive ions and negative ions from an ion generating element;
  an emission direction changing mechanism for changing a direction of ion emission from the ion generator;
  an emission direction control section for controlling the emission direction changing mechanism so as to cause the direction of ion emission to change in accordance with whether the image forming apparatus is in an operating state or a non-operating state; and
  an emission amount control section for controlling the ion generating element so as to change, in accordance with whether the image forming apparatus is in the operating state or the non-operating state, a ratio between positive ions and negative ions to be emitted from the ion generator so that more negative ions are emitted in the operating state than in the non-operating state.

2. The image forming apparatus as set forth in claim 1, wherein
  while the image forming apparatus is in the operating state, the emission direction control section controls the emission direction changing mechanism so as to set the direction of ion emission from the ion generator to a direction toward the image forming apparatus; and
  while the image forming apparatus is in the non-operating state, the emission direction control section controls the emission direction changing mechanism so as to set the direction of ion emission from the ion generator to a direction opposite to the direction toward the image forming apparatus.

3. The image forming apparatus as set forth in claim 1 wherein
while the image forming apparatus is in the operating state, the emission direction control section controls the emission direction changing mechanism so as to set the direction of ion emission from the ion generator to a direction toward the image forming apparatus; and
while the image forming apparatus is in the non-operating state, the emission direction control section controls the emission direction changing mechanism so as to set the direction of ion emission from the ion generator to a direction toward an indoor space.

4. The image forming apparatus as set forth in claim 1, wherein
the emission amount control section controls the ion generating element so as to cause the ion generator to emit negative ions while the image forming apparatus is in the operating state, and
the emission amount control section controls the ion generating element so as to cause the ion generator to emit negative ions and positive ions while the image forming apparatus is in the non-operating state.

5. The image forming apparatus as set forth in claim 1, wherein, in response to an operation of a copy start key, the emission amount control section controls the ion generating element so as to increase an amount of negative ions to be emitted by the ion generator.

6. The image forming apparatus as set forth in claim 1, wherein, upon reception of a print request, the emission amount control section controls the ion generating element so as to increase an amount of negative ions to be emitted from the ion generator.

7. The image forming apparatus as set forth in claim 1, wherein the ion generator is attached to the image forming apparatus via a supporting member in such a manner that the ion generator is positioned above the image forming apparatus.

8. The image forming apparatus as set forth in claim 7, wherein the supporting member is provided so as to be protruding upward at one corner section on a back surface side of the image forming apparatus and so as to support one end to the ion generator.

9. An image forming apparatus for forming an image on a recording material, comprising:
an ion generator, provided outside a main body of the image forming apparatus, for generating and emitting positive ions and negative ions;
an emission direction changing section for changing, in accordance with whether the image forming apparatus is in an operating state or a non-operating state, a direction of ion emission from the ion generator; and
an emission amount adjusting section for changing, in accordance with whether the image forming apparatus is in the operating state or the non-operating state, a ratio between positive ions and negative ions to be emitted from the ion generator so that more negative ions are emitted in the operating state than in the non-operating state wherein, in response to an operation of a copy start key, the emission amount adjusting section increases an amount of negative ions to be emitted by the ion generator.

10. The image forming apparatus as set forth in claim 9, wherein, upon reception of a print request, the emission amount adjusting section increases an amount of negative ions to be emitted from the ion generator.

* * * * *